United States Patent [19]

Miller et al.

[11] Patent Number: 5,629,263

[45] Date of Patent: May 13, 1997

[54] SYNERGISTIC ANTIMICROBIAL COMPOSITIONS CONTAINING POLY (HEXAMETHYLAMMONIUM) CHLORIDE

[75] Inventors: James J. Miller, Norcross; Geoffrey A. Brown, Lithonia; E. LeRoy Lines, Atlanta, all of Ga.

[73] Assignee: Bio-Lab, Inc., Decatur, Ga.

[21] Appl. No.: 632,003

[22] Filed: Apr. 15, 1996

Related U.S. Application Data

[62] Division of Ser. No. 163,118, Dec. 7, 1993, Pat. No. 5,508,250.

[51] Int. Cl.$^6$ .......................... A01N 33/00; A01N 33/12; A01N 35/00; A01N 37/52
[52] U.S. Cl. .......................... 504/158; 504/159; 514/635; 514/642
[58] Field of Search .......................... 514/635, 342; 504/158, 159

[56] References Cited

U.S. PATENT DOCUMENTS

| | | | |
|---|---|---|---|
| 4,253,971 | 3/1981 | MacLeod et al. | 210/759 |
| 4,455,250 | 6/1984 | Frazier | 252/106 |
| 5,041,463 | 8/1991 | Whitekettle et al. | 514/634 |
| 5,142,002 | 8/1992 | Metzner | 514/642 |
| 5,371,083 | 12/1994 | Hollis et al. | 514/241 |

OTHER PUBLICATIONS

F.C. Kull, P.C. Eisman, H.D. Sylwestrowicz and R.L. Mayer, "Mixtures of Quaternary Ammonium Compounds and Long-Chain Fatty Acids as Antifungal Agents," *American Society for Microbiology*, vol. 9, pp. 538–541 (1961).

*Primary Examiner*—Allen J. Robinson
*Attorney, Agent, or Firm*—Woodard, Emhardt, Naughton, Moriarty & McNett

[57] ABSTRACT

Methods for inhibiting microbial growth in aqueous systems by the use of synergistic mixtures comprising poly (hexamethylammonium) chloride and at least one compound selected from the group consisting of poly (iminoimidocarbonyliminoimidocarbonyliminohexamethylene hydrochloride ("PHMB"), dodecylguanidine hydrochloride ("DGH") and poly[oxyethylene (dimethylimino) ethylene-(dimethylimino) ethylene dichloride] ("PDED"). Antimicrobial compositions comprising the synergistic mixture and a carrier are also disclosed.

2 Claims, No Drawings

SYNERGISTIC ANTIMICROBIAL COMPOSITIONS CONTAINING POLY (HEXAMETHYLAMMONIUM) CHLORIDE

This application is a division of application Ser. No. 08/163,118, filed Dec. 7, 1993, now U.S.Pat. No. 5,508,250.

FIELD OF THE INVENTION

The present invention relates generally to antimicrobial compositions, and more particularly to new antimicrobial compositions comprising synergistic mixtures of Poly (hexamethylammonium) chloride ("Q6/6") and certain other biocides.

BACKGROUND OF THE INVENTION

The use of antimicrobial agents to eliminate or control the growth of various microorganisms is widely known. For example, it is known to use antimicrobial agents to control the growth of microorganisms in a variety of industrial processes, including those relating to the paint, pulp, paper, oil, rubber and tobacco industries; to use antimicrobials in commercial settings, particularly to disinfect contaminated surfaces; and to include antimicrobial agents in a wide variety of household goods such as foods, cosmetics and toiletries.

To accommodate such needs, a variety of antimicrobial agents are known. However, despite the many commercially available antimicrobials, no single agent is entirely suitable for every application. Problems with efficacy, safety, environmental acceptability and cost make certain antimicrobials more or less suitable for a particular application.

Certain advantages of using a combination of antimicrobial agents in a single application are known in the art. For example, it is known that a combination of agents may provide an antimicrobial which is effective against a broader spectrum of microbes than are controlled by a single agent alone. This broad spectrum coverage is especially useful in industrial applications where a diversity of microorganisms is frequently encountered.

It is also known that using a combination of antimicrobials can make the agents more effective when the antimicrobial composition is to be used over an extended course of treatment. One reason for this increased effectiveness is that a combination of antimicrobials is less susceptible to having the targeted microbes develop a resistance to the antimicrobial agent because microorganisms cannot readily adapt to more than one active ingredient at a time.

Moreover, using a combination of agents enables one to take advantage of antimicrobials which have different, yet complementary, pysiochemical properties.

In light of this background, there is a continuing need for unique antimicrobial compositions comprising combinations of antimicrobial agents. The present invention addresses this need.

SUMMARY OF THE INVENTION

Briefly describing one aspect of the present invention, there is provided a synergistic composition for inhibiting microbial growth. The synergistic composition comprises poly(hexamethylammonium) chloride and at least one compound selected from the group consisting of poly (iminoimidocarbonyliminoimidocarbonyliminohexamethylene hydrochloride ("PHMB"), dodecylguanidine hydrochloride ("DGH") and poly[oxyethylene (dimethylimino) ethylene-(dimethylimino) ethylene dichloride] ("PDED"). These synergistic compositions may further include a carrier to provide the antimicrobial agent in liquid form.

Another aspect of the invention provides a method of inhibiting growth of microbes. The method comprises contacting the microbes with an antimicrobially effective amount of a syuergistic composition comprising poly (hexamethylammonium) chloride and a compound (i.e. one or more compounds) selected from the group consisting of poly (iminoimidocarbonyliminoimidocarbonyliminohexamethylene hydrochloride ("PHMB"), dodecylguanidine hydrochloride ("DGH") and poly[oxyethylene (dimethylimino) ethylene-(dimethylimino) ethylene dichloride] ("PDED").

It is one object of tile present invention to provide new, synergistic mixtures for use as antimicrobial agents.

Another object of the invention is to provide methods for inhibiting microbial growth using the synergistic mixtures.

Related objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications and applications of the principles of the invention as described herein being contemplated as would normally occur to one skilled in the art to which the invention relates.

The present invention relates to synergistic mixtures of poly(hexamethylammonium) chloride ("Q6/6") and at least one compound selected from the group consisting of poly (iminoimidocarbonyliminoimidocarbonyliminohexamethylene hydrochloride ("PHMB"), dodecylguanidine hydrochloride ("DGH") and poly[oxyethylene (dimethylimino) ethylene-(dimethylimino) ethylene dichloride] ("PDED"). The synergistic mixtures are active against yeasts such as *Candida albicans*, against molds such as *Aspergillus niger* and against algae such as *Scenedesmus obliquus*.

Concerning the specific components of the synergistic compositions, poly(hexamethylammonium) chloride is a cationic, polyquaternary ammonium compound, specifically 1,6-hexanediamine-N,N,N',N'-tetraamethyl polymer with 1,6-dichlorohexane ("Q6/6"). This, and the other antimicrobials of the present invention are commercially available and/or can be made by procedures known art. Typically, Q6/6 is provided as 50% active ingredient, PHMB is provided as 20% active ingredient, DGH is provided as 33% active ingredient and PDED is provided as 60% active ingredient.

Synergistic combinations of Q6/6 were discovered using the microorganisms listed below. All organisms were purchased from American Type Culture Collection (ATCC) and each strain is catalogued by a numerical identifier.

| Genus and species | Type of Microorganism |
| --- | --- |
| *Candida albicans* ATCC 18804 | Fungus (Yeast) |
| *Aspergillus niger* ATCC 6275 | Fungus (Mold) |
| *Scenedesmus obliquus* ATCC 11457 | Alga |

Each of these organisms is important in industrial and or recreational applications. *Candida albicans* is a pathogenic yeast that can cause infections of the skin and mucous membranes. Candida and *Aspergillus niger* are industrially significant microorganisms especially in the areas of paints, cosmetics, preservatives, etc. While *Candida albicans* might be introduced into recreational waters by infected individuals, neither it nor Aspergillus has been implicated in pool or spa biofouling. Three forms of algae are commonly found in swimming pools: green algae, blue green and mustard. Scenedesmus is a non-filamentous, green alga, which commonly inhabits soil. Because it is often found in soil, it can contaminate sources such as swimming pools.

Before synergism can be determined, the MIC's (minimal inhibitory concentration) of the individual biocides must be established. The MIC is defined as the lowest concentration which completely inhibits microbial growth for the duration of the experiment (48 hours for bacteria, 72 hours for fungi and 2 weeks for algae). Individual MIC's were determined during initial screening on microtiter plates or in sterile tubes (for algae). MIC's from initial screens were needed to determine the appropriate biocide concentrations used during synergism testing.

In order to determine the MIC's on microtiter plates, 50 µl of phosphate water is added to each row in columns 2 –12 (FIG. 1). Next, 100 µl of a biocide is added to column 1 (A–H). Fifty microliters of the biocide is removed from column 1 and serially diluted from columns 2–11 using an eight tip pipettor (octapette). Finally, 50 µl of microbial inoculum is added to columns 1–11 (all rows) and column 12 (row A and E only). Column 12 serves as the row for sterility and viability controls.

Bacterial and yeast inoculua contain about $1\times10^9$ colony forming units (cfu) per ml and are prepared in ⅕ strength Nutrient and Sabouraud Dextrose broth, respectively. Bacterial microtiter plates are incubated at 37° C. for 48 hours. Yeast plates are incubated at 25° C. for 72 hours. Molds contain ca $1\times10^7$ spores/ml and are prepared in ⅕ strength Sabouraud Dextrose broils. Like the yeast, it is incubated for 72 hours at 25° C. Algae are prepared in Allen's Medium and incubated under fluorescent lights (12 hours on/12 hours off) at ambient temperature (ca 23°C.) for two weeks. Prior to testing, algae cultures are standardized to 85–95%T at 490 nm. Allen's Medium is a standard milieu in which to culture algae and consists of:

| Recipe for Allen's Medium | |
| --- | --- |
| | g/liter |
| $K_2HPO_4$ | 0.25 |
| $CaCl_2.2H_2O$ | 0.066 |

-continued

| Recipe for Allen's Medium | |
| --- | --- |
| | g/liter |
| $MgSO_4.7H_2O$ | 0.513 |
| $FeCl_3$ | 0.003 |
| $NaNO_3$ | 1.00 |
| $NH_4Cl$ | 0.05 |

Synergism tests are conducted 96 well microtiter plates, and every test is run in duplicate (FIG. 1). Using an octapette, 50 µl of sterile, phosphate buffered distilled water is added to columns 2 through 10 (rows A–H). Next, 100 µl of biocide "A" is added to column 1 (rows A–H) with the octapette. Using the octapette, 50 µl of the mixture is removed from each well in column 1 and serial dilutions are made beginning at column 2 and ending at column 7. Fifty microliters of biocide "B" is added in row A (1–8). After mixing thorougly, serial dilutions are made beginning at row B and ending at row G, columns 1–8 (serial dilutions reduce biocide concentrations by 50% in adjoining wells. See FIG. 2). At this point, rows 1–10 (A–H) contain 50 µl. Finally, 50 µl of bacterial, fungal or algal inoculum are placed into columns 1–9, rows A through H. The concentration of biocide "A" is highest in row A and lowest in row G. The test is invalidated if the viability control does not grow, or if there is growth in the sterility control wells.

FIG. 1

|   | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A |   |   |   |   |   |   |   | B | V | S |   |   |
|   |   |   |   |   |   |   |   | I — I — T |   |   |   |   |
| B |   |   |   |   |   |   |   | O | A | E |   |   |
|   |   |   |   |   |   |   |   | C — B — R |   |   |   |   |
| C |   |   |   |   |   |   |   | I | I | I |   |   |
|   |   |   |   |   |   |   |   | D — L — L |   |   |   |   |
| D |   |   |   |   |   |   |   | E | I | I |   |   |
|   |   |   |   |   |   |   |   | T — T |   |   |   |   |
| E |   |   |   |   |   |   |   | B | Y | Y |   |   |
| F |   |   |   |   |   |   |   | M |   |   |   |   |
|   |   |   |   |   |   |   |   | I |   |   |   |   |
| G |   |   |   |   |   |   |   | C |   |   |   |   |
| H | BIOCIDE A MIC (H1–H7) | | | | | | |   |   |   |   |   |

Synergism describes the situation in which the combined biocidal activity of two antimicrobials is greater than the sum of their individual activities. The method used to determine synergism was described by Kull et al. using the following equation:

$$\frac{QA}{Qa} + \frac{QB}{Qb} = \text{Synergism Index } (SI)$$

In the equation, Qa and Qb are the concentrations of biocide A or B which acting alone, produce an endpoint. QA and QB are the concentrations of A or B in the mixture that produce an endpoint. Endpoints were defined by determining the Minimum Inhibitory Concentration (MIC) for each microorganism listed above. All synergism MIC experiments were performed in 96 well tissue culture plates or occasionally in sterile tubes (algae). A maximum of two biocides were tested on each of these sterile, multi-well dishes. Each plate was used to simultaneously determine the MIC's of the individual biocides as well as the MIC's of various combinations of the respective antimicrobials. Synergism indices are calculated for each combination of biocides A and B. When the synergism index (SI) is less than 1, synergism exists. When the SI equals 1, there is additivity. When the SI is greater than 1, antagonism exists. In order for synergism to exist (SI less than 1), the MIC of each biocide within the combination must be less than the MIC's of the individual biocides.

FIG. 2 describes what the synergism indices would be if biocides A and B each had MIC's of 1. The SI values have been calculated for each well on a hypothetical microtiter plates. The test itself is qualitative since results are interpreted on the presence or lack of growth.

FIG. 2

BIOCIDE A (H1–H7)
BIOCIDE B (8A–8G)

STERILITY CONTROL

GR (GROWTH)   NG (NO GROWTH)

The synergistic combinations of Q6/6 with PHMB, DGH and PDED disclosed herein are effective against microbes that are notable for water treatment and other applications. Minimum inhibitory concentration analyses were performed in the appropriate growth milieu for each organism. In all cases, "A" and "a" refer to Q6/6 concentrations. "B" and "b" refer always denote the other antimicrobial (PHMB, DGH or PDED) in the synergistic couple. Each endpoint listed below was confirmed at least once by repeat experiments. The data are presented in the tables below.

TABLE 1

PHMB

| Microorganism | Qa | Qb | QA | QB | SI |
|---|---|---|---|---|---|
| Scenedesmus obliquus | 0.50 | 0.25 | 0.125 | 0.125 | 0.75 |
|  |  |  | 0.063 | 0.125 | 0.63 |
|  |  |  | 0.125 | 0.063 | 0.50 |
|  |  |  | 0.125 | 0.125 | 1.25 |
|  |  |  | 0.25 | 0.125 | 1.00 |
| Aspergillus niger | 15.6 | 1.95 | 7.80 | 0.49 | 0.75 |
|  |  |  | 3.90 | 0.98 | 0.75 |
|  |  |  | 7.80 | 0.98 | 1.00 |
| Candida albicans | 15.6 | 0.98 | 7.80 | 0.25 | 0.75 |
|  |  |  | 3.90 | 0.49 | 0.75 |
|  |  |  | 1.95 | 0.49 | 0.63 |

TABLE 1-continued

PHMB

| Microorganism | Qa | Qb | QA | QB | SI |
|---|---|---|---|---|---|
|  |  |  | 0.98 | 0.49 | 0.56 |
|  |  |  | 7.80 | 0.49 | 1.00 |

TABLE 2

DGH

| Microorganism | Qa | Qb | QA | QB | SI |
|---|---|---|---|---|---|
| Scenedesmus obliquus | 0.50 | 0.25 | 0.25 | 0.063 | 0.75 |
|  |  |  | 0.25 | 0.125 | 1.00 |
|  |  |  | 0.25 | 0.031 | 0.63 |
| Asperigillus niger | 15.6 | 1.95 | 3.9 | 0.98 | 0.75 |
|  |  |  | 1.95 | 0.98 | 0.63 |
|  |  |  | 0.98 | 0.98 | 0.56 |
|  |  |  | 7.80 | 0.98 | 1.00 |

TABLE 3

DDED

| Microorganism | Qa | Qb | QA | QB | SI |
|---|---|---|---|---|---|
| Candida albicans | 7.80 | 0.49 | 3.90 | 0.13 | 0.75 |
|  |  |  | 3.90 | 0.06 | 0.63 |
|  |  |  | 1.95 | 0.25 | 0.75 |
|  |  |  | 3.90 | 0.25 | 1.00 |

The synergistic compositions disclosed herein are preferably dissolved or otherwise incorporated in a liquid carrier prior to use but may also be added directly to aqueous systems. Although a wide variety of carriers may be used, preferred carriers include water and alcohol, particularly ethyl or isopropyl alcohol.

When in a liquid carrier, the concentration of active ingredients together may be any concentration and is limited only by the amounts that can be advantageously incorporated in the carrier used. For example, where a composition in solution form is desired, the concentration of actives will of course be limited by the solubility of the actives in the particular carrier employed. In preferred cases, the actives together will comprise up to about 50%, most often about 20% to about 40%, of the liquid composition, with the carrier comprising the remainder of the compositions.

Reference will now be made to specific examples using the processes described above. It is to be understood that the examples are provided to more completely describe preferred embodiments, and that no limitation to the scope of the invention is intended thereby.

EXAMPLE 1

A synergistic composition according to the present invention can be made by dissolving Q6/6 and poly(iminoimidocarbonyliminoimidocarbonyliminohexamethylene hydrochloride ("PHMB") together in water at room temperature. Alternatively, the active ingredients can be added to the media to be treated from separate solutions to achieve the same synergistic effect. A wide range of ratios of the two active ingredients can be used, depending on the microorganism to be controlled. For example, to control the growth of *Scenedesmus obliquus*, the ratio of Q6/6 to PHMB may be as low as 1:2. To control growth of *Aspergillus niger*, the ratio of Q6/6 to PHMB may be 4:1. Preferred ratios of Q6/6 to PHMB for use with other microorgaisms typically lie in the range of about 31:1 to about 2:1.

EXAMPLES 2–3

Further synergistic compositions according to the present invention are made by dissolving Q6/6 and/or dodecylguanidine hydrochloride ("DGH") and poly[oxyethylene (dimethylimino) ethylene-(dimethylimino) ethylene dichloride] ("PDED"). Again, a wide range of ratios of two active ingredients can be used, depending on several factors including the microorganism to be controlled. For example, preferred ratios of Q6/6 to the other antimicrobial is generally are about 4:1 to about 8:1 for DGH and about 8:1 to about 65:1 for PDED.

The antimicrobial compositions described above can be seen to exhibit synergistic activity with respect to a variety of common microorganisms. However, the examples disclosed herein should not be considered to disclose all possible microorganisms which may be controlled by the synergistic combinations, nor should the identified ranges be viewed as limiting in nature. All synergistic antimicrobial combinations of the identified ingredients are intended to be within the scope of the present invention, and all antimicrobial uses thereof are intended to be claimed.

I claim:

1. A synergistic composition for inhibiting microbial growth comprising synergistic amounts of between about 88.6% and about 98.5% poly(hexamethylammonium) chloride and between about 1.5% and about 11.4% of poly (oxyethylene (dimethylimino) ethylene-(dimethylimino) ethylene dichloride) ("PDED").

2. A synergistic composition according to claim 1, wherein the weight ratio of poly(hexamethylammonium) chloride to PDED is in the ratio of about 65:1 to about 8:1.

* * * * *

UNITED STATES PATENT AND TRADEMARK OFFICE
CERTIFICATE OF CORRECTION

PATENT NO. : 5,629,263

DATED : May 13, 1997

INVENTOR(S) : James J. Miller et al.

Page 1 of 2

It is certified that error appears in the above-indentified patent and that said Letters Patent is hereby corrected as shown below:

In col. 1, line 24, please change "houseliold" to --household--.

In col. 2, line 2, please change "syuergistic" to --synergistic--.

In col. 2, line 8, please change "dimethylirnino" to --dimethylimino--.

In col. 2, line 10, please change "tile" to --the--.

In col. 2, line 31, please change "iminoimidocarbonylliminoimidocarbonylimino-hexamethylene" to --iminoimidocarbonyliminoimidocarbonyliminohexamethylene--.

In col. 2, line 41, please change "tetraamethyl" to --tetramethyl--.

In col. 2, line 44, please insert --to the-- after "known".

In col. 2, line 65, please italicize "Candida".

In col. 3, line 2, please italicize "Aspergillus".

In col. 3, line 5, please italicize "Scenedesmus".

In col. 3, line 53, please change "broils" to --broth--.

In col. 4, line 11, please insert --in-- before "96".

In col. 6, Table 2, please change "Asperigillus" to --Aspergillus--.

In col. 6, Table 3, please change "DDED" to --PDED--.

UNITED STATES PATENT AND TRADEMARK OFFICE
CERTIFICATE OF CORRECTION

PATENT NO.  : 5,629,263
DATED       : May 13, 1997
INVENTOR(S) : James J. Miller et al.

It is certified that error appears in the above-indentified patent and that said Letters Patent is hereby corrected as shown below:

In col. 8, line 1, please change "microorgaisms" to --microorganisms--.

In col. 8, line 9, please insert --the-- before "two".

In col. 8, line 34, please change "ratio" to --range--.

Signed and Sealed this

Twenty-fifth Day of November, 1997

Attest:

BRUCE LEHMAN

*Attesting Officer*      Commissioner of Patents and Trademarks